(12) United States Patent
Bylsma

(10) Patent No.: US 6,319,220 B1
(45) Date of Patent: Nov. 20, 2001

(54) PHACOEMULSIFICATION APPARATUS

(76) Inventor: Stephen S. Bylsma, 175 Pioneer Cir., Arroyo Grande, CA (US) 93420

( * ) Notice: Subject to any disclaimer, the term of this patent is extended or adjusted under 35 U.S.C. 154(b) by 0 days.

(21) Appl. No.: 09/453,563

(22) Filed: Dec. 3, 1999

(51) Int. Cl.[7] ................................................. A61B 17/20
(52) U.S. Cl. ............................................ 604/22; 606/107
(58) Field of Search .................. 604/22, 27, 35, 604/118, 119, 120; 606/107

(56) References Cited

U.S. PATENT DOCUMENTS 5,370,602 * 12/1994 Kepley .
5,406,503 * 4/1995 Williams, Jr. et al. .
5,836,897 * 11/1998 Sakurai et al. .

* cited by examiner

Primary Examiner—Manuel Mendez
Assistant Examiner—Catherine Serke
(74) Attorney, Agent, or Firm—William L. Klima; Law Offices of William L. Klima, P.C.

(57) ABSTRACT

The present invention is directed to a phacoemulsification apparatus configured for random pulse mode operation. Specifically, the phacoemulsification apparatus is electrically controlled to operate an ultrasonic hand piece, and thus a tip of a phacoemulsification needle in a random pulse mode.

10 Claims, 5 Drawing Sheets

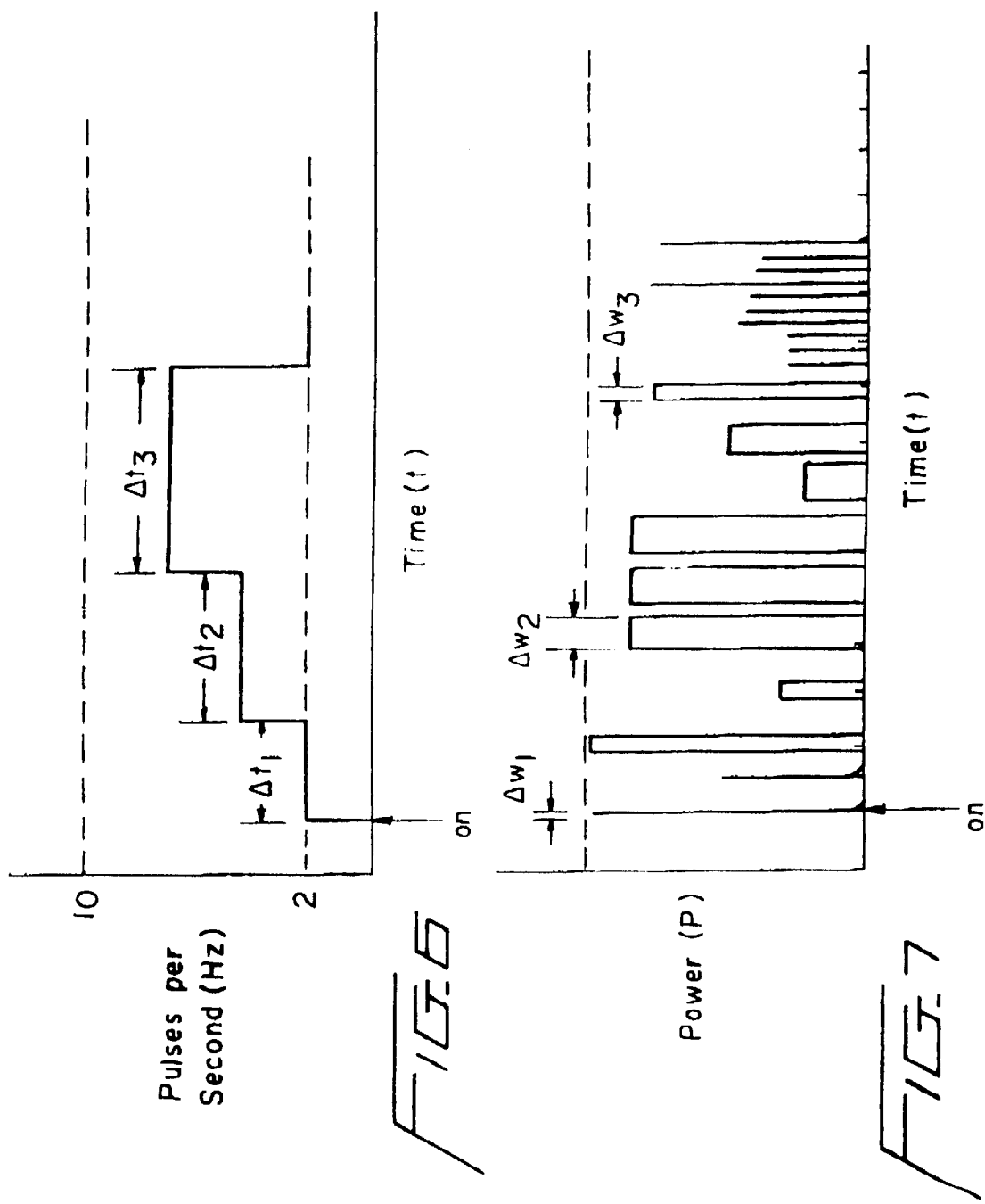

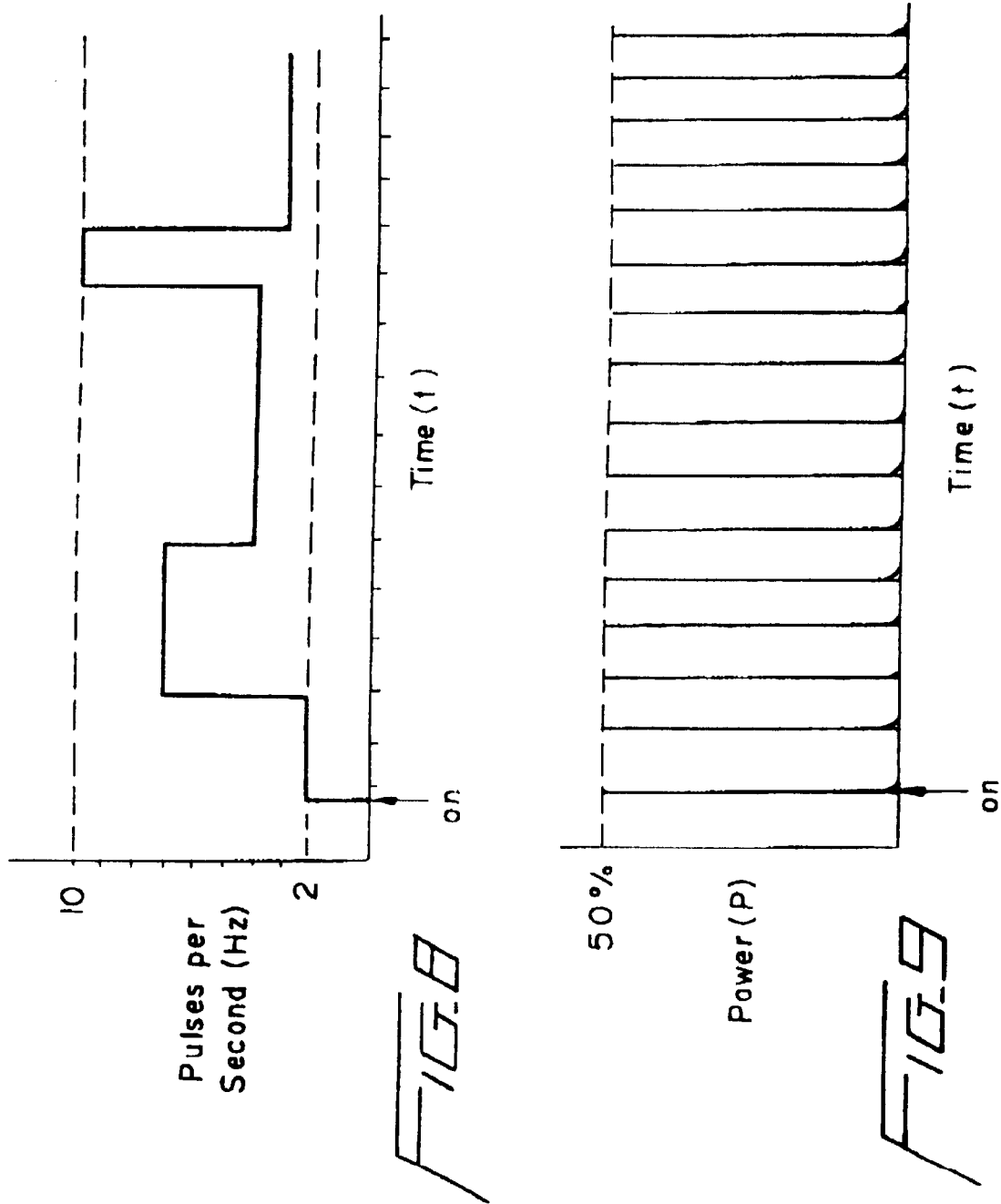

PHACOEMULSIFICATION APPARATUS

FIELD OF THE INVENTION

The present invention is directed to a phacoemulsification apparatus. More specifically, the present invention is directed to a phacoemulsification apparatus configured to provide a random pulse mode of operation of an ultrasonic hand piece, and thus a tip of a phacoemulsification needle.

BACKGROUND OF THE INVENTION

The phacoemulsification apparatus is used in eye surgery for removing the natural crystalline lens of the eye. The conventional phacoemulsification apparatus includes a hand piece having an ultrasonic transducer for driving a hollow phacoemulsification needle. The hand piece is provided with an irrigation line and an aspiration line, and is configured for directing the flow of irrigation fluid through the needle into the eye. The hand piece is also provided with a sleeve surrounding the phacoemulsification needle, and is further configured for aspirating fluid to flow from the eye into a lumen defined between the needle and sleeve.

During cataract surgery, a small incision is made in the eye and the hand piece is manipulated so that the phacoemulsification needle with the sleeve is inserted through the small incision. After capsulorrhexis, the ultrasonically driven phacoemulsification needle is placed in contact or near contact with the cateracteous natural lens or lens nucleus and vibrated ultrasonically to begin erosion of the structure of the lens nucleus. As the structure of the lens nucleus is destroyed, the lens debris is vacuumed into the needle cannula, through the hand piece, and then out of the hand piece through the aspiration line.

During the phacoemulsification process, the ultrasound energy applied to the lens nucleus by the phacoemulsification needles creates a repulsive force which tends to push free-floating fragments away from the tip of the phacoemulsification needle. The aspiration line connected to the hand piece provides aspiration or "flow" that draws fluid into the tip of the phacoemulsification needle via a pump (e.g. peristaltic pump, venturi, vacuum pump, etc., or combinations thereof), and overcomes the repulsive force to some extent. However, there is still observed many instanes where nuclear fragments are "pushed" away from the tip of the phacoemulsification needle.

The conventional phacoemulsification apparatus includes a source for irrigation fluid (e.g. one or more bottles of irrigation fluid) and a source of vacuum (e.g. peristaltic pump, venturi, vacuum pump, etc., or combinations thereof). The conventional phacoemulsification apparatus also includes a power supply and control for driving the ultrasonic hand piece, and thus the tip of the phacoemulsification needle. Typically, the conventional phacoemulsification apparatus includes a console containing the power supply, control (e.g. analog and/or microprocessor), peristaltic pump, and other components. The hand piece is electrically connected to the hand piece by a cable, and fluidly connected to the irrigation fluid supply and vacuum source by a tubing set.

The conventional phacoemulsification apparatus has electronics configured for driving the ultrasonic hand piece at different power levels based on the position on a foot pedal control. Some conventional phacoemulsification apparatus are configured for providing a "pulse mode" believed to be effective for breaking up the lens nucleus more effectively. However, in the conventional "pulse mode", the pulses are constant. Specifically, the pulses achieve approximately the same power level, the same pulse width or duty cycle, and the pulses are equally spaced apart timewise.

To minimize the "pushing" or repulsive effect of ultrasound waves propagating from the tip of the phacoemulsification needle on the nuclear fragments, the "pulse-mode" was created to energize the ultrasonic hand piece, and thus tip of the phacoemulsification tip intermittently. Accordingly, the repulsive force effect is only applied intermittently, allowing the aspiration (flow) rate to keep the free nuclear fragment(s) closer to the ultrasound tip for quicker removal. However, repulsion of a nuclear fragment is still frequently noted even with operation of the pulse-mode, especially when the pulse-rate is high. Low pulse-rates have been used to enhance prevention of occlusions with some success, but the prevention of enhanced occlusions is counterproductive to certain techniques of phacoemulsification.

Further, the conventional single setting pulse-mode, such as six (6) pulses per second, sets up standing waves relative to the tip of the phacoemulsification needle, which negates the desired effect of pulse-mode. These standing wave create not only ultrasound repulsions, but fluid repulsion as well, thereby further hindering efficient nuclear removal.

To maximize the proximity of free nuclear fragments to the phacoemulsification tip and thereby improve the speed and efficiency of phacoemulsification, new innovations to the conventional pulse mode are needed.

SUMMARY OF THE INVENTION

A first object of the present invention is to provide an improved phacoemulsification apparatus.

A second object of the present invention is to provide a phacoemulsification apparatus configured for drawing and maintaining free nuclear fragments at or near the tip of the phacoemulsification needle.

A third object of the present invention is to provide a phacoemulsification apparatus configured for providing a random pulse mode of operation of the ultrasonic hand piece.

A fourth object of the present invention is to provide a phacoemulsification apparatus configured for providing a random pulse mode of operation of the tip of a phacoemulsification needle.

A fifth object of the present invention is to provide a phacoemulsification apparatus configured for providing a random pulse mode of operation wherein the number of pulses of a pulse sequence varies randomly.

A sixth object of the present invention is to provide a phacoemulsification apparatus configured for providing a random pulse mode of operation wherein the pulses per second varies randomly.

A seventh object of the present invention is to provide a phacoemulsification apparatus configured for providing a random pulse mode of operation wherein the pulse width or duty cycle varies randomly.

An eighth object of the present invention is to provide a phacoemulsification apparatus configured for providing a random pulse mode of operation wherein the power supply for driving the ultrasonic hand piece varies randomly.

A ninth object of the present invention is to provide a phacoemulsification apparatus configured for providing a random pulse mode of operation wherein the power output of the ultrasonic hand piece varies randomly.

A tenth object of the present invention is to provide a phacoemulsification apparatus configured for providing a random pulse mode of operation wherein the power output of the tip of the phacoemulsification needle varies randomly.

An eleventh object of the present invention is to provide a phacoemulsification apparatus configured for providing fluidics at or near the tip of a phacoemulsification needle, which fluidics varies randomly.

A twelfth object of the present invention is to provide a phacoemulsification apparatus configured for providing a random pulse mode of operation in combination with providing fluidics at or near the tip of a phacoemulsification needle, which fluidics varies randomly.

The phacoemulsification apparatus according to the present invention is configured to provide a "random-pulse mode" for the operation of the ultrasonic hand piece. The random-pulse mode is designed to avoid the creation of ultrasound standing waves at or near the tip of the phacoemulsification needle by varying the pulse rate rapidly. This prevents standing waves and a recurring pattern of ultrasound around the tip of the phacoemulsification needle, and promotes removal of free nuclear fragments by minimizing the repulsive force of the ultrasound. Furthermore, the fluid drawn into the phacoemulsification tip is enhanced by vortex and eddies formed in the region around the randomly pulsing tip of the phacoemulsification needle. The combination of no standing waves and increased drawing of fluid in the tip of the phacoemulsification needle that results from random pulse mode phacoemulsification greatly increases the efficiency, speed, and safety of phacoemulsification.

BRIEF DESCRIPTION OF THE DRAWINGS

FIG. 6 is a table of Pulses per Second verses Time (t) for illustrating the random pulse mode of operation of the phacoemulsification apparatus according to the present invention.

FIG. 7 is a table of Power (P) verses Time (t) for illustrating the random pulse mode of operation of the phacoemulsification apparatus according to the present invention.

FIG. 8 is a table of Pulses per Second verses Time (t) for illustrating the random pulse mode of operation of the phacoemulsification apparatus according to the present invention.

FIG. 9 is a table of Power (P) verses Time (t) for illustrating the random pulse mode of operation of the phacoemulsification apparatus according to the present invention.

DETAILED DESCRIPTION OF PREFERRED EMBODIMENTS

The term "random pulse mode" refers to a mode of operation of the phacoemulsification apparatus, in particular the mode of operation of the ultrasonic hand piece, and more particular the resulting mode of operation of the tip of the phacoemulsification needle. Random pulse mode ("RPM") means controlling the operation of the phacoemulsification apparatus, in particular the ultrasonic hand piece to cause the phacoemulsification needle to operate by pulsing and vibrate ultrasonically in a random manner. Specifically, the number of pulses, the amplitude of the pulses, the pulse width or pulse duty cycle of each successive pulse, the time separation between successive pulses, and other parameters of the output of the tip of the phacoemulsification needle can be changed or varied to provide a random pulse mode according to the present invention.

For example, one or more electrical parameters (e.g. voltage, current, frequency, impedance, capacitance, etc.) used in controlling the ultrasonic hand piece can be turned on, turned off, varied and/or changed randomly to result in the hand piece, and thus the phacoemulsification needle, operating in a random pulse mode according to the present invention.

The amount or degree of randomness of the pulsing of the hand piece, and thus phacoemulsification needle, may be slightly random to completely random mathematically or statistically. The amount or degree of randomness may be constant or also varied during operation of the ultrasonic hand piece to provide more complicated type randomness.

Figure 1:
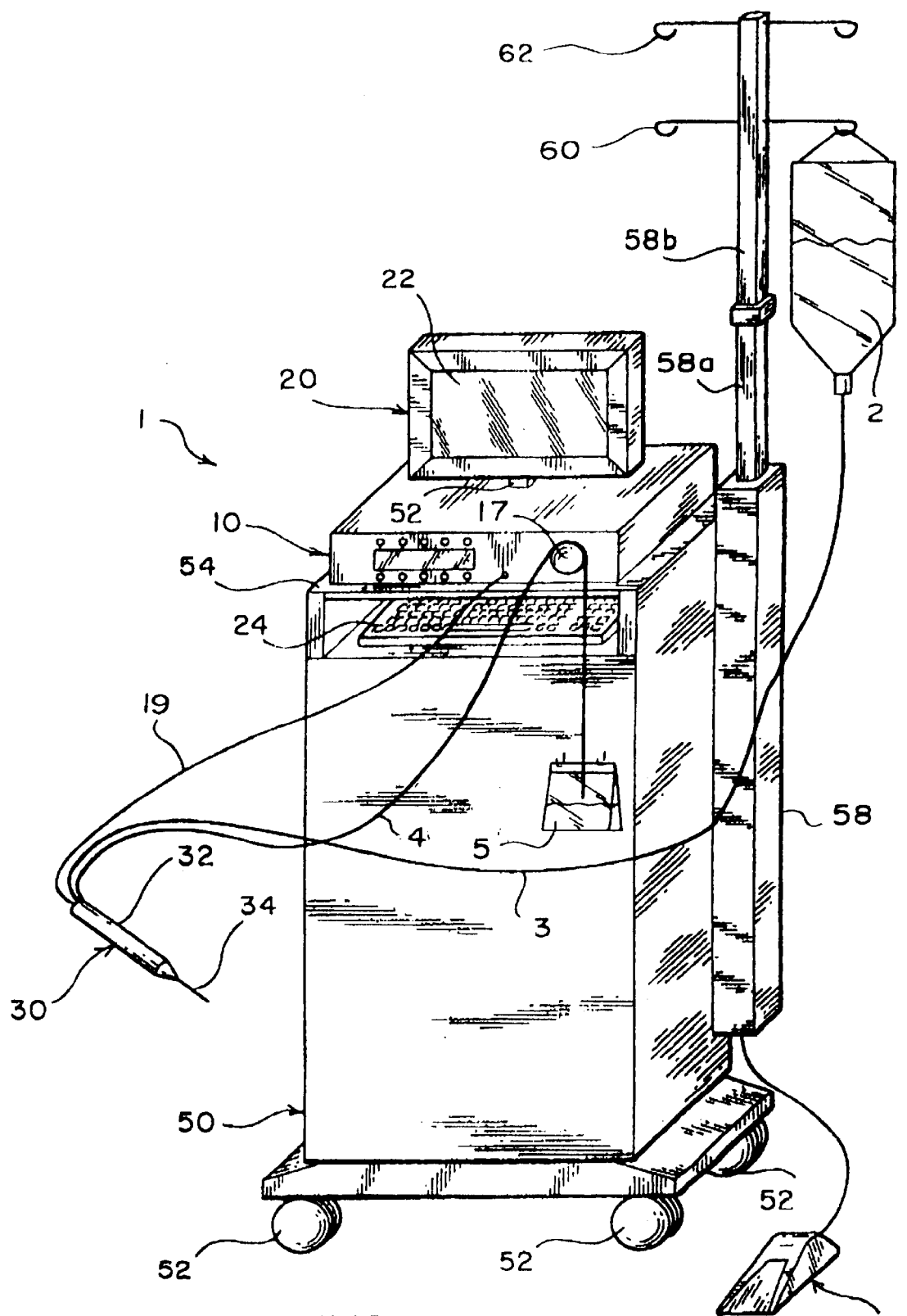
FIG. 1 is a perspective view of a phacoemulsification apparatus according to the present invention.

A phacoemulsification apparatus 1 according to the present invention is shown in FIG. 1. The phacoemulsification apparatus 1 is provided with an irrigation fluid supply 2 (e.g. bottle or bag) and a replaceable tubing set including irrigation tubing 3 and aspiration tubing 4. Further, the phacoemulsification apparatus includes the main components of a control console 10, personal computer 20, hand piece 30, foot pedal 40 and movable stand 52.

Figure 2:
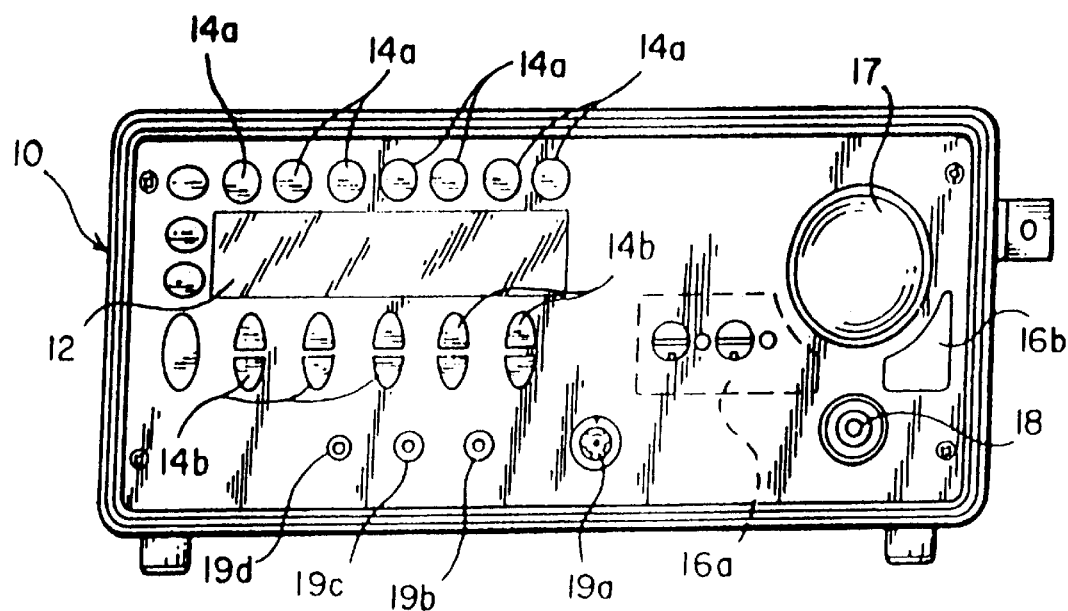
FIG. 2 is a front elevational view of the control console of the phacoemulsification apparatus shown in FIG. 1.
Figure 3:
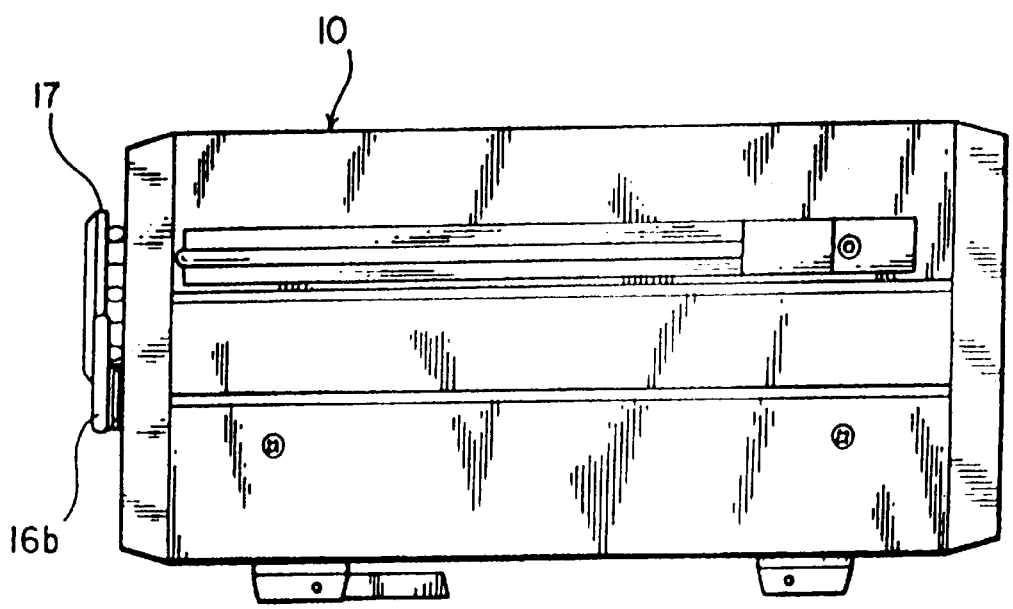
FIG. 3 is a side elevational view of the control console shown in FIG. 2.

The control console 10 (FIG. 2) is provided with display 12, touch control buttons 14a and 14b, removable tubing cassette 16a, and a stationary tubing holder 16b. The control console 10 also includes a peristaltic pump 17, and a vacuum sensor 18 provided on a front panel thereof The front panel is provided with an ultrasonic supply jacket 19a for connecting a cable 19 leading to the hand piece 30.

Figure 4:
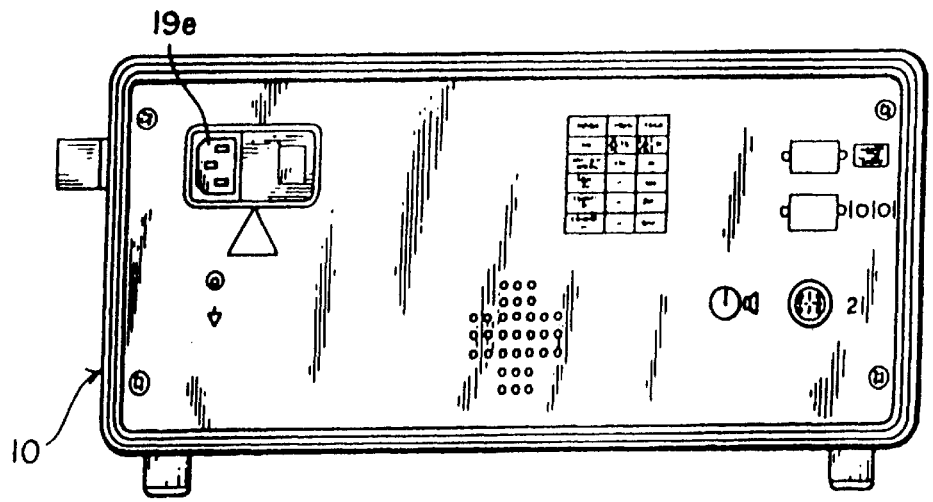
FIG. 4 is a back elevational view of the control console shown in FIG. 2.
Figure 5:
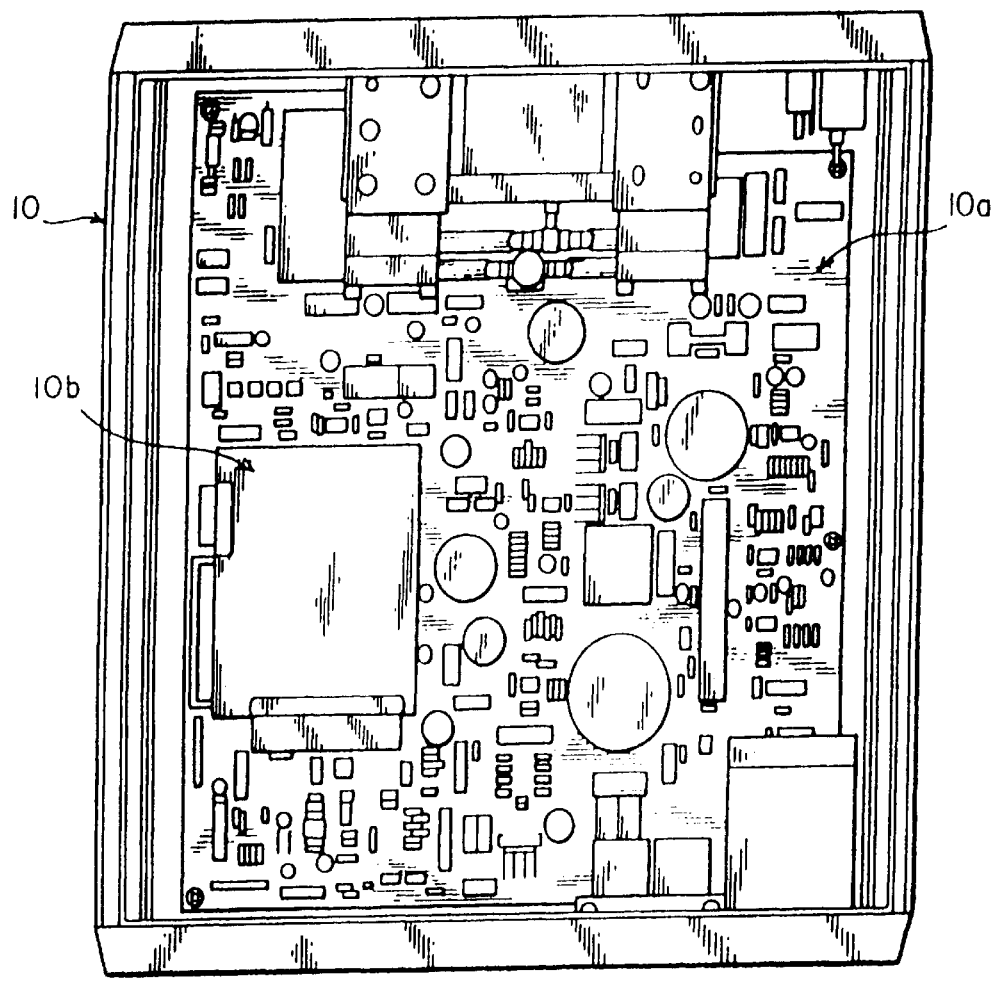
FIG. 5 is a broken away top elevational view of the control console shown in FIG. 2 revealing the electronic components thereof.

The back panel of the control console 10 is provided with a conventional AC power jack (FIG. 4). The control console 10 contains a variety of electrical components, including circuit board 10a and microprocessor controller 10b (FIG. 5).

The personal computer 20 is provided with an integral screen 22 and remote keyboard 24 wired to the personal computer 20. The personal computer 20 is supported above the console 10. The personal computer 20 is programmed to communicate with the control console 10. The control console 10 can also be provided with voice activation.

The phacoemulsification hand piece 30 can be a conventional ultrasonic type hand piece 30, including an ultrasonic transducer (not shown) located within housing 32. An ultrasonically driven phacoemulsification needle 34 is connected to the hand piece 30, and provided with an outer resilient silicone sleeve.

A foot pedal 40 is electrically connected to the console 10. The foot pedal 40 is a multi-position type foot pedal configured to control operation of the phacoemulsification apparatus 10.

OPERATION

The phacoemulsification apparatus 1 is configured electronically to drive the ultrasonic hand piece 30, and thus the phacoemulsification needle 34 in the random pulse mode. Specifically, the circuit board 10a provided with microprocessor controller 10b can be programmed with a specifically designed software algorithm to drive the ultrasonic hand piece 30, and thus the phacoemulsification needle in the random pulse mode.

A particularly effective random pulse mode can be achieved by driving the phacoemulsification hand piece 30 by varying the number of pulses per second at a constant power level. Alternatively, or in combination, the power level can be controlled and varied in a random or non-random manner. Further, the number of pulses in a sequence at a predetermined setting of number of pulses per second can change in number higher or lower in the next sequence of pulses. Further, the number of pulses per second may be varied between preset limits. The number of pulses in a sequence at a predetermined setting of number of pulses per second is preferably one (1) to five (5) pulse sequences and more preferably one (1) to four (4) pulse sequences. If the sequence reaches over five (5) pulses in a row, the operation of the tip of the phacoemulsification needle becomes too constant (i.e. not random enough) to be effective for the random pulse mode of operation.

In the operation of the phacoemulsification apparatus 10 shown in FIG. 6, there exists random durations of time periods $\Delta t_1$, $\Delta t_2$ and $\Delta t_3$ at different levels of Pulses per Second (Hz). In FIG. 7, random pulse widths $\Delta w_1$, $\Delta w_2$, and $\Delta w_3$ are illustrated. Thus, this particular random pulse mode includes two (2) different independent operational parameters each having randomly changing magnitudes.

Likewise, the fluidics at or near the tip of the phacoemulsification needle can be varied randomly, alone or in combination with the random pulse mode. The random fluidics can be provided in various manners. For example, the speed of the peristaltic pump can be controlled so that the chive signal to the peristaltic pump is randomly pulsed. Alternatively, the flow through the irrigation and/or aspiration lines can be controlled to vary in a random manner (e.g. providing electrically controlled flow valves in irrigation and/or aspiration lines and/or vent(s) to irrigation and/or aspiration lines).

EXAMPLE 1

The preset limits of the microprocessor 10b were programmed by external controllers on the front panel 12 of the control console 10. The lower preset limit was set at two (2) pulses per second and the higher preset limit was set at ten (10) pulses per second. The power level was set at fifty percent (50%). The power of the ultrasonic hand piece 30 was then controlled to be on at fifty percent (50%) power and then turned off to zero percent (0%) power.

The microprocessor 10b was programed to carry out an ongoing random sequences of pulses. For example, the following was a possible pulse sequence for operation of the random pulse mode:

2 pulses at 2 Hertz (Hz, pulses per second), followed by, 3 pulses at 7 Hz, followed by, 5 pulses at 4 Hz, followed by, 1 pulse at 10 Hz, followed by, 4 pulses at 3 Hz, and so on.

The real time interrupt between pulses was programmed around 100 milliseconds.

A table showing the Pulses per Second (Hz) verses Time (t) is shown in FIG. 8, and a table showing the independent pulses with Power (P) verses Time (t) is shown in FIG. 9.

I claim:

1. A phacoemulsification apparatus, comprising:

a power supply;

a control device for controlling said power supply; and an ultrasonic hand piece including a phacoemulsification needle, said ultrasonic hand piece being electrically connected to said power supply, wherein said control device is configured for operating said ultrasonic hand piece in a random pulse mode, said control device configured to randomly vary a number of pulses in a sequence of pulses.

2. The apparatus according to claim 1, wherein said number of pulses per sequence is from one to five.

3. The apparatus according to claim 1, wherein said number of pulses is more preferably from one to four.

4. The apparatus according to claim 1, wherein said control device is configured to randomly vary a level of pulses per sec (Hz).

5. The apparatus according to claim 4, wherein the level of pulses per sec (Hz) is randomly varied after each pulse sequence.

6. The apparatus according to claim 4, wherein said control device is configured to randomly vary the pulse width.

7. The apparatus according to claim 6, wherein said control device is configured to randomly vary the pulse width after each pulse sequence.

8. The apparatus according to claim 1, wherein said control device is configured to randomly vary the pulse width.

9. The apparatus according to claim 8, wherein said control device is configured to randomly vary the pulse width after each pulse sequence.

10. The apparatus according to claim 1, wherein at least one of the following parameters is varied randomly, including at least one selected from the group consisting of:

(i) the number of random pulses of a pulse sequence varies randomly;

(ii) the pulses per second varies randomly;

(iii) the pulse width or duty cycle varies randomly;

(iv) the power supply for driving the ultrasonic hand piece varies randomly;

(v) the power output of the ultrasonic hand piece varies randomly;

(vi) the power output of the tip of the phacoemulsification needle varies randomly; and (vii) the fluidics at or near the tip of a phacoemulsification needle varies randomly.

* * * * *